US011452563B2

(12) United States Patent
Govari et al.

(10) Patent No.: US 11,452,563 B2
(45) Date of Patent: Sep. 27, 2022

(54) ADAPTING IRRIGATION RATE IN RADIOFREQUENCY (RF) ABLATION IN RESPONSE TO CONTACT-FORCE VARIATION

(71) Applicant: BIOSENSE WEBSTER (ISRAEL) LTD., Yokneam (IL)

(72) Inventors: Assaf Govari, Haifa (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 319 days.

(21) Appl. No.: 16/403,865

(22) Filed: May 6, 2019

(65) Prior Publication Data

US 2020/0352641 A1    Nov. 12, 2020

(51) Int. Cl.
*A61B 18/14*    (2006.01)
*A61B 18/12*    (2006.01)
(Continued)

(52) U.S. Cl.
CPC ...... *A61B 18/1492* (2013.01); *A61B 18/1206* (2013.01); *A61B 90/06* (2016.02);
(Continued)

(58) Field of Classification Search
CPC ........ A61B 2090/065; A61B 2018/064; A61B 2018/00011; A61B 2018/00029; A61B 2018/00035; A61B 18/1492; A61B 90/06; A61B 18/1206; A61B 2018/00351; A61B 2018/00577; A61B 2018/00791; A61B 2018/00839; A61B 2218/002; A61B 2018/00744; A61B 2018/00357;
(Continued)

(56) References Cited

U.S. PATENT DOCUMENTS 6,083,223 A * 7/2000 Baker ............... A61B 18/1445
606/49
9,962,217 B2   5/2018 Govari
(Continued)

FOREIGN PATENT DOCUMENTS

| EP | 3292831 A1 | 3/2018 |
| EP | 3360499 A1 | 8/2018 |
| RU | 2542088 C2 | 1/2014 |

OTHER PUBLICATIONS

European Search Report for corresponding EPA No. 20173010.8 dated May 10, 2020.
U.S. Appl. No. 16/288,838, filed Feb. 28, 2019.

*Primary Examiner* — Linda C Dvorak
*Assistant Examiner* — Nicholas S Borsch
(74) *Attorney, Agent, or Firm* — Dergosits & Noah LLP; Todd A. Noah

(57) ABSTRACT

A method of body tissue ablation includes generating an ablation signal and providing the ablation signal to an ablation probe that is in contact with tissue. Irrigation fluid is delivered to the ablation probe, for applying the irrigation fluid in a vicinity of the tissue while the ablation signal is applied to the tissue. Signals are received from the ablation probe, which are indicative of an estimated instantaneous contact force that is exerted by the ablation probe against the tissue. A flow rate of the irrigation fluid is adapted responsively to the estimated instantaneous contact force.

14 Claims, 2 Drawing Sheets

(51) Int. Cl.
 *A61B 90/00* (2016.01)
 *A61B 18/00* (2006.01)
(52) U.S. Cl.
 CPC ........... *A61B 2018/00351* (2013.01); *A61B 2018/00577* (2013.01); *A61B 2018/00791* (2013.01); *A61B 2018/00839* (2013.01); *A61B 2090/065* (2016.02); *A61B 2218/002* (2013.01)
(58) Field of Classification Search
 CPC .......... A61B 18/12; A61B 2018/00642; A61B 18/14; A61B 2018/00696; A61B 2018/00702; A61B 2018/00708; A61B 2018/00714; A61B 2018/0072; A61B 2018/00738; A61B 2018/00761; A61B 2018/00773; A61B 2018/00886; A61B 2018/00779; A61B 2018/00785
 See application file for complete search history.

(56) References Cited

U.S. PATENT DOCUMENTS

| | | | |
|---|---|---|---|
| 2009/0287092 | A1 | 11/2009 | Leo et al. |
| 2014/0336640 | A1* | 11/2014 | Beeckler ............ A61B 18/1492 606/41 |
| 2016/0143696 | A1 | 5/2016 | Govari et al. |
| 2016/0213282 | A1 | 7/2016 | Leo et al. |
| 2017/0014181 | A1* | 1/2017 | Bar-Tal ............... A61B 18/1492 |
| 2019/0069949 | A1* | 3/2019 | Vrba .................... A61B 17/122 |
| 2021/0145534 | A1* | 5/2021 | Kulstad .................. A61F 7/123 |

* cited by examiner

ADAPTING IRRIGATION RATE IN RADIOFREQUENCY (RF) ABLATION IN RESPONSE TO CONTACT-FORCE VARIATION

FIELD OF THE INVENTION

The present invention relates generally to radiofrequency (RF) ablation, and particularly to cardiac RF ablation.

BACKGROUND OF THE INVENTION

Techniques for controlling RF ablation were previously proposed in the patent literature. For example, U.S. Patent Application Publication 2016/0213282 describes a method and apparatus that utilize a force-time integral for real time estimation of lesion size in catheter-based ablation systems. The apparatus measures the force exerted by a contact ablation probe on a target tissue and integrates the force over an energization time of the ablation probe. The force-time integral can be calculated and utilized to provide an estimated lesion size (depth, volume and/or area) in real time. The force-time integral may also account for variations in the power delivered to the target tissue in real time to provide an improved estimation of the lesion size. In one embodiment, the force metric can be used as feedback to establish a desired power level delivered to the probe to prevent steam popping. In still other embodiments, the control system can be adapted to increase irrigation, in addition or in place of decreasing or disabling energization.

As another example, U.S. Pat. No. 9,962,217 describes tissue ablation systems and methods in which a cardiac catheter incorporates a pressure detector for sensing a mechanical force against the distal tip when engaging an ablation site. Responsively to the pressure detector, a controller computes an ablation volume according to relationships between the contact pressure against the site, the power output of an ablator, and the energy application time. The system applies a specified dosage of energy for an application time and at a power level to the tissue for ablation thereof, wherein at least one of the application time of the dosage and the power level depend on the mechanical force. A monitor may dynamically display the progress of the ablation by varying a visual indication of the computed ablation volume.

SUMMARY OF THE INVENTION

An embodiment of the present invention provides a method of body tissue ablation, including generating an ablation signal and providing the ablation signal to an ablation probe that is in contact with tissue. Irrigation fluid is delivered to the ablation probe, for applying the irrigation fluid in a vicinity of the tissue while the ablation signal is applied to the tissue. Signals are received from the ablation probe, which are indicative of an estimated instantaneous contact force that is exerted by the ablation probe against the tissue. A flow rate of the irrigation fluid is adapted responsively to the estimated instantaneous contact force.

In some embodiments, the method further includes monitoring a temperature of the tissue and adapting the flow rate of irrigation responsively to the monitored temperature.

In some embodiments, adapting the flow rate includes increasing or decreasing the flow rate while maintaining the ablation signal at a maximal power level for a shortest duration of ablation.

In an embodiment, the duration of ablation and the maximal power level are predetermined constants.

In another embodiment, the method further includes, while applying the ablation signal, continuously evaluating an ablation index and stopping the ablation signal upon the ablation index reaching an ablation-index threshold.

In some embodiments, the ablation index depends on a power level of the ablation signal.

In some embodiments, the ablation index depends on the instantaneous contact force.

In an embodiment, adapting the flow rate responsively to the estimated instantaneous contact force includes increasing or decreasing the flow rate responsively to a respective estimated increase or decrease in the instantaneous contact force.

There is additionally provided, in accordance with an embodiment of the present invention, a system for body tissue ablation, the system including a generator, an irrigation module, and a processor. The generator is configured to generate an ablation signal and to provide the ablation signal to an ablation probe that is in contact with tissue. The irrigation module is configured to deliver irrigation fluid to the ablation probe for applying the irrigation fluid in a vicinity of the tissue while the ablation signal is applied to the tissue. The processor is configured to receive from the ablation probe signals indicative of an estimated instantaneous contact force that is exerted by the ablation probe against the tissue, and to control the irrigation module to adapt a flow rate of the irrigation fluid responsively to the estimated instantaneous contact force.

The present invention will be more fully understood from the following detailed description of the embodiments thereof, taken together with the drawings in which:

DETAILED DESCRIPTION OF EMBODIMENTS

Overview

Figure 1:
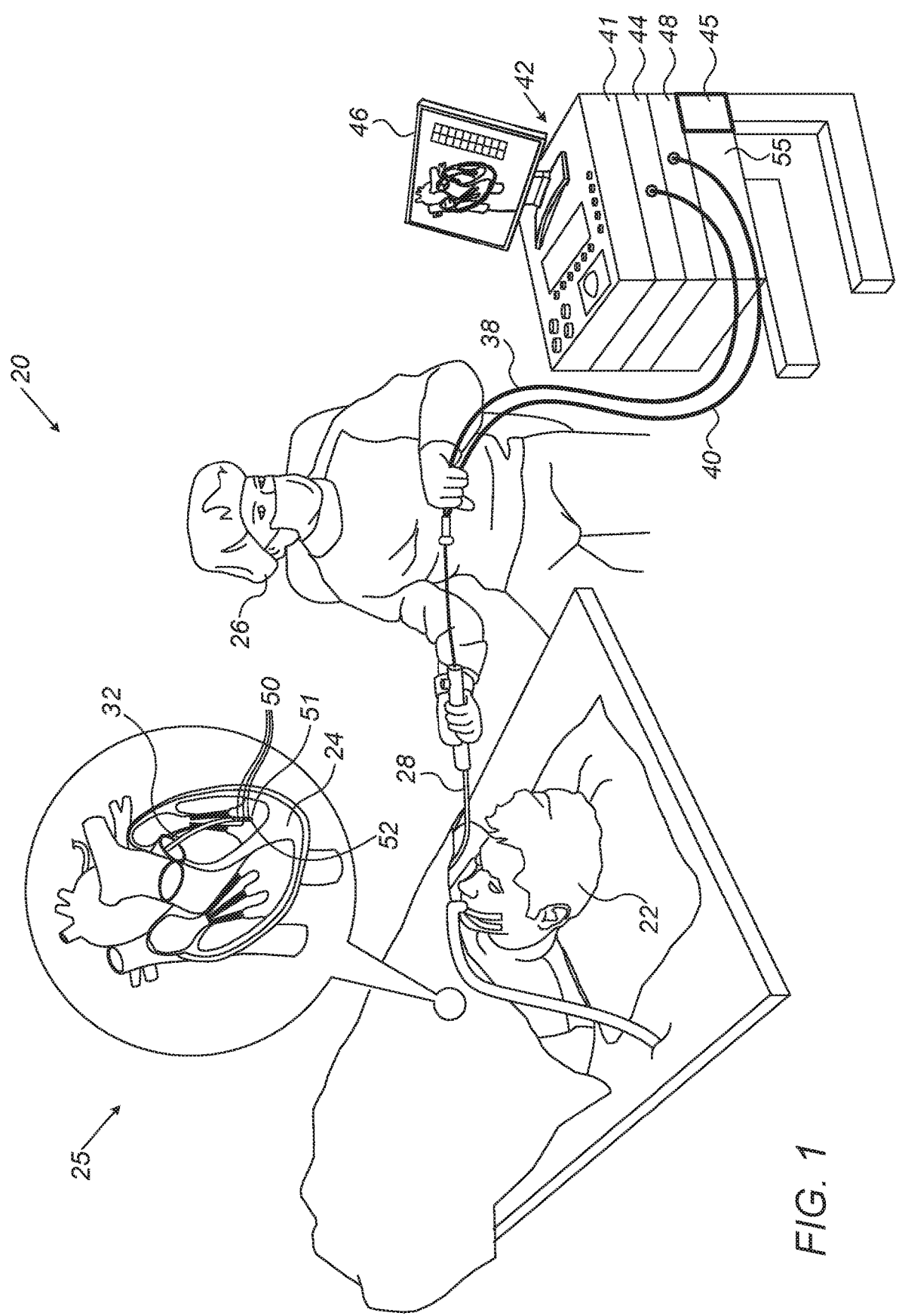
FIG. 1 is a schematic, pictorial illustration of a system for cardiac radiofrequency (RF) ablation therapy, in accordance with an embodiment of the present invention.

To control an ablation process aimed at creating a lesion of a given size, cardiac ablation systems, such as radiofrequency (RF) ablation systems, may vary the irrigation rate, the ablation (e.g., RF) power input, and the duration of ablation, while ensuring that the temperature of the ablated tissue does not exceed a maximum value. Nevertheless, the resulting lesion size may vary due to variation in the mechanical force with which an ablation electrode is in contact with tissue during the ablation. Therefore, unless compensated for, a varying contact force may cause an uncontrolled and/or inaccurate outcome of the RF ablation.

Embodiments of the present invention that are described hereinafter provide improved methods and systems for RF ablation. An underlying assumption in the disclosed techniques is that the only variables during RF ablation for a specific lesion size within a preset time are the instantaneous (i.e., momentary) contact force on the tissue being ablated, the irrigation flow rate, and tissue temperature. Assuming that tissue temperature is approximately constant, some embodiments keep the delivered power substantially constant, and compensate for measured changes in instantaneous contact force by adapting the irrigation flow rate.

Typically, for the ablation process to continue under elevated instantaneous contact-force conditions, a processor running an algorithm for the ablation would command an increase in the irrigation flow rate within an allowable range. If the instantaneous contact force decreases, the processor running an algorithm for the ablation would command a reduction in the irrigation flow rate so that the ablation process remains effective.

In other embodiments, changes in monitored temperature are also compensated for by adapting the irrigation flow rate. Typically, the processor monitors the temperature of the tissue and commands the irrigation flow rate to adapt (e.g., increase or decrease) responsively to the monitored temperature, and in some embodiments, responsively to a respective increase or reduction in the monitored temperature.

In some embodiments, the disclosed method comprises the steps of (a) inserting a probe, such as a catheter, into a body of a living subject, (b) putting the probe into contact with a tissue in the body, (c) presetting a power output level and time of ablation, (d) presetting a range of allowable flow rate of irrigation, (e) measuring an instantaneous contact force, (f) generating an ablation signal and providing the ablation signal to an ablation probe that is in contact with tissue (i.e., depositing into tissue the preset amount of power via one or more ablation electrodes of the probe), (g) delivering irrigation fluid to the ablation probe, for applying the irrigation fluid in a vicinity of the tissue while the ablation signal is applied to the tissue, (h) receiving from the ablation probe signals indicative of an estimated instantaneous contact force that is exerted by the ablation probe against the tissue, and (j) adapting the flow rate of the irrigation fluid responsively to the estimated instantaneous contact force.

In some embodiments, a system for body tissue ablation is provided, which includes (i) a memory, which is configured to store a value of target amount of ablation energy needed to create a specified lesion in tissue in a body of a patient, and further stores respective values of maximal power level and shortest duration of ablation (ii) an irrigation module configured to deliver irrigation fluid to the ablation probe, wherein the ablation probe is configured to: (iia) make contact with tissue, (iib) apply the irrigation fluid in a vicinity of the tissue. The ablation probe further includes means for sensing an instantaneous contact force that is exerted by the probe against the tissue.

The provided system further includes a generator, which is configured to generate the ablation signal and provide the ablation signal to the ablation probe, and a processor, which is configured to: (a) receive from the ablation probe signals indicative of an estimated instantaneous contact force that is exerted by the ablation probe against the tissue, (b) and control the irrigation module to adapt a flow rate of the irrigation fluid responsively to the estimated instantaneous contact force.

The disclosed RF ablation technique, which compensates for a variation in instantaneous contact force that an electrode exerts on tissue by responsively varying the flow rate of irrigation, may allow maintaining a maximal RF power level for the shortest duration of ablation, and by so may improve a clinical outcome of a catheter-based RF ablation procedure.

System Description

FIG. 1 is a schematic, pictorial illustration of a system for cardiac radiofrequency (RF) ablation therapy, in accordance with an embodiment of the present invention. Typically, a memory 45 of system 20 stores numerous ablation protocols for different clinical scenarios, such as a protocol described in FIG. 2.

A physician 26 inserts a catheter 28 through a blood vessel into a chamber of a heart 24 of a subject 22, and manipulates the catheter so that a distal end 32 of the catheter contacts the endocardium in an area that is to be treated. A tip electrode 51 of catheter 28, seen in inset 25, comprises one or more contact force sensors 50.

After positioning distal end 32 at an ablation site, and ensuring that the tip is in contact with the endocardium, operator 26 actuates an RF energy generator 44 in a control console 42 to supply RF energy via a cable 38 to distal end 32. Meanwhile, an irrigation module 55, comprising a controllable irrigation pump 48, supplies a cooling fluid, such as normal saline solution, via a tube 40 and a lumen in catheter 28 to the distal end. Typically, both before and during the ablation, a display 46 displays values of the ablation parameters, such as those listed in Table I below, to physician 26.

In order to operate system 12, a processor 41 controls an irrigation module 55 as further described below. In particular, processor 41 runs a dedicated algorithm as disclosed herein, included in FIG. 2, that enables processor 41 to perform the disclosed steps, as further described below.

Operation of the RF energy generator and the irrigation pump may be coordinated in order to give the appropriate volume of irrigation during ablation, so as to cool the tip of the catheter and the tissue without overloading the heart with irrigation fluid. Each contact force sensor 50 provides feedback to console 42 for use in controlling the irrigation flow rate.

In an embodiment, during ablation, one or more sensor temperatures 52 located in tip electrode 51 of catheter 28 may sense tissue temperature and transmit a temperature-indicative signal to processor 41 for analysis and use.

Processor 41 uses software stored in a memory 45 to operate system 20. The software may be downloaded to processor 41 in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, included in FIG. 2, that enables processor 41 to perform the disclosed steps, as further described below.

Although the pictured embodiment relates specifically to the use of a tip ablation device for ablation of heart tissue, the methods described herein may alternatively be applied in ablation devices comprising multiple ablation electrodes, in cases where the operation of irrigation with each electrode is independently controlled by processor 41. In an alternative embodiment, processor 41 controls irrigation flow shared by all electrodes. Using feedback on the maximal instantaneous contact force among all electrodes, the processor adapts the common flow rate of irrigation.

Figure 2:
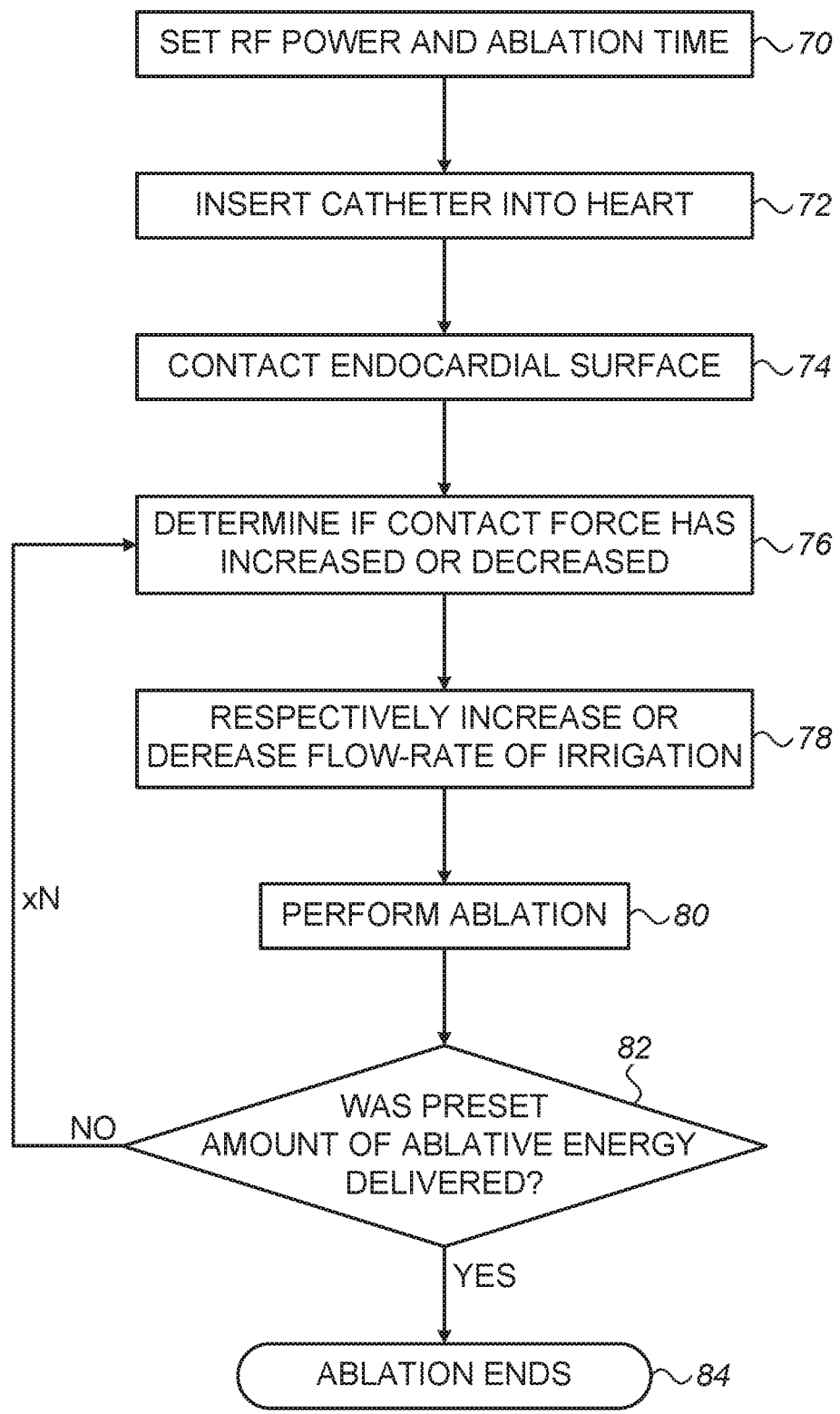
FIG. 2 is a flow chart that schematically describes steps of an algorithm performed in operation of the RF ablation system of FIG. 1, according to an embodiment of the present invention.

Adapting Irrigation Rate in Radiofrequency (RF) Ablation in Response to Contact-Force Variation FIG. 2 is a flow chart that schematically describes steps of an algorithm performed in operation of RF ablation system of FIG. 1, according to an embodiment of the present invention. The process begins in a parameter range presetting step 70, during which physician 26 presets ablation power and time (i.e., duration). Such a step may involve generating multiple protocols for different clinical scenarios, where such protocols are saved, for example, in memory 45 of system 20.

In an embodiment, the values/ranges are set as shown in Table I:

TABLE I

| Parameter | Value/Range |
|---|---|
| Preset maximal power level | 50 W-90 W |
| Preset ablation time | 2 s-20 s |
| Sampling rate of contact force | 5 Hz-70 Hz |
| Irrigation flow rate | 2-30 ml/min |

Parameter range setting step 70 is implemented before physician 26 performs an ablation. In particular, ablation time (i.e., the duration of ablation) and the maximal power level are predetermined constants. However, the values/ranges of power, time, and flow rate may be set differently, for example, with a lesion depth target. Tables for low depth (less than 2 mm), medium depth (2 mm-3.5 mm), high depth (3.5 mm-5.0 mm), and extra depth (more than 5.0 mm) are described in a U.S. patent application Ser. No. 16/288,838, filed Feb. 28, 2019, entitled "Energy-Guided Radiofrequency (RF) Ablation," which is assigned to the assignee of the present patent application and whose disclosure is incorporated herein by reference.

In some embodiments, the duration, T, of ablation is determined during the ablation by providing a maximally allowable ablation index (AI), i.e., an ablation index threshold (AIT), that is an integral of power level times contact force over a duration, and solving the integral to extract the duration as a function of a given AIT input. The processor is configured to continuously evaluate the AI during the ablation process, and to stop the ablation when the AI reaches the AIT.

One example for an equation of AIT is described in a U.S. Patent Application Publication 2017/0014181, which is assigned to the assignee of the present patent application and whose disclosure is incorporated herein by reference. This example ablation index threshold (AIT), denoted AIT1, has the form, $AIT1=(k*\int_0^T CF^\alpha(t)*P^\beta(t)dt)^\gamma$, where the integral is over duration T, of a product of the contact force, CF, raised to a first non-unity exponent, $\alpha$, and the power, P, raised to a second non-unity exponent, $\beta$, k is a constant of proportionality and $\gamma$ is a third non-unity exponent. The values of $\alpha$, $\beta$, $\gamma$ and k are determined by methods disclosed in the aforementioned U.S. Patent Application Publication 2017/0014181. In an alternative embodiment, the processor uses a second equation for AIT, denoted AIT2, to determine the duration of ablation, where the second AIT is given by $AIT2=k*\int_0^T P(t)dt$.

At the beginning of an ablation session, in a catheter introduction step 72, physician 26 inserts catheter 28 into a desired location in heart 24, using a catheter position tracking system incorporated into system 20.

Next, physician 26 makes physical contact between electrode tip 51 and endocardial tissue, at an electrode-tissue contact step 74. Processor 41 receives contact-force indicative signals from sensors on catheter 28 and determines the instantaneous contact force and/or whether the contact force increased or decreased, at contact force determination step 76.

At an irrigation step 78, processor 41 controls irrigation module 55 to increase or decrease the irrigation flow rate responsively to a determined respective increase or reduction in instantaneous mechanical force. For example, if the instantaneous contact force has increased, then processor 41 directs irrigation module 55 to momentarily increase the irrigation flow so that the rate of heat removal by irrigation will match an increase in deposited heat due to the better physical contact between electrode and tissue. On the other hand, if the instantaneous contact force has decreased, meaning less heat is deposited and tissue may be too cooled, then processor 41 directs irrigation module 55 to momentarily decrease the irrigation flow.

In RF delivery step 80, physician 26 operates system 20, with the parameter values selected in step 70, in order to perform the ablation of electrode 51. Display 46 of system 20 may be configured to display to physician 26, by methods which are known in the art, the progress of the RF delivery to the electrode.

During the RF delivery procedure processor 41 monitors the instantaneous contact force using N repeated measurements, by looping back to step 78. The number of repetitions N is calculated by the product of ablation time and contact-force sampling rate in Table I, wherein y example N=20. Processor 41 responsively commands irrigation module 55 to modify the irrigation flow rate according to the instantaneous contact force, by repeating step 78.

At each repetition, processor 41 checks if the preset amount of ablative energy was delivered, at an ablation energy monitoring step 82. At an ablation ending step 84, processor ends ablation after the ablation energy resulting from power and time presets in step 70 is achieved, or the indicated time has elapsed.

The example flow chart shown in FIG. 2 is chosen purely for the sake of conceptual clarity. The sampling rate of contact force is brought by way of example, where a higher rate might be used. The present embodiment also comprises additional steps of the algorithm, such as checking tissue temperature, which have been omitted from the disclosure herein purposely on order to provide a more simplified flow chart.

Although the embodiments described herein mainly address cardiac application, the methods and systems described herein can also be used in ablating other organs of the body such as kidneys (e.g., for renal denervation) and lungs.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method of body tissue ablation, the method comprising:
generating an ablation signal and providing the ablation signal to an ablation probe that is in contact with tissue;
delivering irrigation fluid to the ablation probe, for applying the irrigation fluid in a vicinity of the tissue while the ablation signal is applied to the tissue;

receiving from the ablation probe signals indicative of an instantaneous contact force that is exerted by the ablation probe against the tissue; and adjusting the flow rate of the irrigation fluid responsively and iteratively to correspond to a determined increase or decrease in the instantaneous contact force and respective increase or decrease in heat applied to the tissue, wherein the irrigation flow rate is increased when it is determined that the instantaneous contact force has increased such that rate of heat removal from the tissue matches an increase in heat due to the increased instantaneous contact force and the irrigation flow rate is decreased when it is determined that the instantaneous contact force has decreased such that the rate of heat removal matches a decrease in heat due to the decreased instantaneous contact force; and determining, at each iteration, whether a preset amount of ablative energy was delivered, and stopping ablation in response to a determination that the preset amount of ablative energy was delivered.

2. The method according to claim 1, and comprising monitoring a temperature of the tissue and adapting the flow rate of irrigation responsively to the monitored temperature.

3. The method according to claim 1, wherein adjusting the flow rate comprises increasing or decreasing the flow rate while maintaining the ablation signal at a maximal power level for a shortest duration of ablation.

4. The method according to claim 3, wherein the duration of ablation and the maximal power level are predetermined constants.

5. The method according to claim 3, and comprising, while applying the ablation signal, continuously evaluating an ablation index and stopping the ablation signal upon the ablation index reaching an ablation-index threshold.

6. The method according to claim 5, wherein the ablation index depends on a power level of the ablation signal.

7. The method according to claim 5, wherein the ablation index depends on the instantaneous contact force.

8. A system for body tissue ablation, the system comprising:

a generator, configured to generate an ablation signal and to provide the ablation signal to an ablation probe that is in contact with tissue;

an irrigation module, configured to deliver irrigation fluid to the ablation probe, for applying the irrigation fluid in a vicinity of the tissue while the ablation signal is applied to the tissue; and a processor, configured to:

receive from the ablation probe signals indicative of an instantaneous contact force that is exerted by the ablation probe against the tissue; and control the irrigation module to adjust a flow rate of the irrigation fluid responsively and iteratively to correspond to a determined increase or decrease in the instantaneous contact force and respective increase or decrease in heat applied to the tissue, wherein the irrigation flow rate is increased when it is determined that the instantaneous contact force has increased such that rate of heat removal from the tissue matches an increase in heat due to the increased instantaneous contact force and the irrigation flow rate is decreased when it is determined that the instantaneous contact force has decreased such that the rate of heat removal matches a decrease in heat due to the decreased instantaneous contact force; and determining, at each iteration, whether a preset amount of ablative energy was delivered, and stopping ablation in response to a determination that the preset amount of ablative energy was delivered.

9. The system according to claim 8, wherein the processor is further configured to monitor a temperature of the tissue and to control the irrigation module to adapt the flow rate responsively to the monitored temperature.

10. The system according to claim 8, wherein the processor is configured to control the irrigation module to adapt the flow rate and maintain the ablation signal at a maximal power level for a shortest duration of ablation.

11. The system according to claim 10, and comprising a memory, which is configured to store the values of the maximal power level and the shortest duration of ablation as predefined constants.

12. The system according to claim 8, wherein the processor is configured to continuously evaluate an ablation index, and to stop the ablation signal upon the ablation index reaching an ablation-index threshold.

13. The system according to claim 12, wherein the ablation index depends on a power level of the ablation signal.

14. The system according to claim 12, wherein the ablation index depends on the instantaneous contact force.

\* \* \* \* \*